(12) United States Patent
Zienert et al.

(10) Patent No.: US 7,421,060 B2
(45) Date of Patent: Sep. 2, 2008

(54) METHOD OF DETERMINING AN ORIENTATION OF A CRYSTAL LATTICE OF A FIRST SUBSTRATE RELATIVE TO A CRYSTAL LATTICE OF A SECOND SUBSTRATE

(75) Inventors: Inka Zienert, Dresden (DE); Jochen Rinderknecht, Dresden (DE); Thorsten Kammler, Ottendorf-Okrilla (DE)

(73) Assignee: Advanced Micro Devices, Inc., Austin, TX (US)

( * ) Notice: Subject to any disclaimer, the term of this patent is extended or adjusted under 35 U.S.C. 154(b) by 0 days.

(21) Appl. No.: 11/744,313

(22) Filed: May 4, 2007

(65) Prior Publication Data

US 2008/0056449 A1    Mar. 6, 2008

(30) Foreign Application Priority Data

Aug. 31, 2006  (DE) .................. 10 2006 041 003

(51) Int. Cl.
*G01N 23/20* (2006.01)

(52) U.S. Cl. .............................. 378/71; 378/73; 378/76
(58) Field of Classification Search .............. 378/70–90
See application file for complete search history.

(56) References Cited

U.S. PATENT DOCUMENTS 6,977,986 B1 *  12/2005  Beanland et al. .............. 378/34

* cited by examiner

*Primary Examiner*—Jurie Yun
(74) *Attorney, Agent, or Firm*—Williams, Morgan & Amerson, P.C.

(57) ABSTRACT

According to an illustrative embodiment disclosed herein, a semiconductor structure comprising a first crystalline substrate and a second crystalline substrate is provided. The semiconductor structure is irradiated with a radiation. Both the first crystalline substrate and the second crystalline substrate are exposed to the radiation. At least one diffraction pattern of a crystal lattice of the first crystalline substrate and a crystal lattice of the second crystalline substrate is measured. A relative orientation of the crystal lattice of the first crystalline substrate and the crystal lattice of the second crystalline substrate is determined from the at least one diffraction pattern.

21 Claims, 7 Drawing Sheets

METHOD OF DETERMINING AN ORIENTATION OF A CRYSTAL LATTICE OF A FIRST SUBSTRATE RELATIVE TO A CRYSTAL LATTICE OF A SECOND SUBSTRATE

BACKGROUND OF THE INVENTION

1. Field of the Invention

The present disclosure generally relates to the fabrication of integrated circuits, and, more particularly, to the formation of semiconductor structures comprising a first substrate and a second substrate having a different orientation.

2. Description of the Related Art

Integrated circuits comprise a large number of individual circuit elements, e.g., transistors, capacitors and resistors. These elements are connected to form complex circuits, such as memory devices, logic devices and microprocessors. The performance of integrated circuits can be improved by increasing the number of functional elements per circuit in order to increase the circuit's functionality and/or by increasing the speed of operation of the circuit elements. A reduction of feature sizes allows the formation of a greater number of circuit elements on the same area, hence increasing the functionality of the circuit, and also reducing signal propagation delays, thus making an increase of the speed of operation of circuit elements possible.

Field effect transistors are typically used as switching elements in integrated circuits. They provide a means to control a current flowing through a channel region located between a source region and a drain region. The source region and the drain region are highly doped. In N-type transistors, the source and drain regions are doped with an N-type dopant. Conversely, in P-type transistors, the source and drain regions are doped with a P-type dopant. The doping of the channel region is inverse to the doping of the source region and the drain region. The conductivity of the channel region is controlled by a gate voltage applied to a gate electrode formed above the channel region and separated therefrom by a thin insulating layer. Depending on the gate voltage, the channel region may be switched between a conductive "on" state and a substantially non-conductive "off" state.

When reducing the size of field effect transistors, it is important to maintain a high conductivity of the channel region in the "on" state. The conductivity of the channel region in the "on" state depends on the dopant concentration in the channel region, the mobility of the charge carriers, the extension of the channel region in the width direction of the transistor and on the distance between the source region and the drain region, which is commonly denoted as "channel length." While a reduction of the width of the channel region leads to a decrease of the channel conductivity, a reduction of the channel length enhances the channel conductivity. An increase of the charge carrier mobility leads to an increase of the channel conductivity.

As feature sizes are reduced, the extension of the channel region in the width direction is also reduced. A reduction of the channel length entails a plurality of issues associated therewith. First, advanced techniques of photolithography and etching have to be provided in order to reliably and reproducibly create transistors having short channel lengths. Moreover, highly sophisticated dopant profiles, in the vertical direction as well as in the lateral direction, are required in the source region and in the drain region in order to provide a low sheet resistivity and a low contact resistivity in combination with a desired channel controllability.

In view of the problems associated with a further reduction of the channel length, it has been proposed to also enhance the performance of field effect transistors by increasing the charge carrier mobility in the channel region. In principle, at least three approaches may be used to increase the charge carrier mobility.

First, the dopant concentration in the channel region may be reduced. Thus, the probability of scattering events of charge carriers in the channel region is reduced, which leads to an increase of the conductivity of the channel region. Reducing the dopant concentration in the channel region, however, significantly affects the threshold voltage of the transistor device. This makes the reduction of dopant concentration a less attractive approach.

Second, the lattice structure in the channel region may be modified by creating tensile or compressive stress. This leads to a modified mobility of electrons and holes, respectively. Depending on the magnitude of the stress, a compressive stress may significantly increase the mobility of holes in a silicon layer, and may also increase the electron mobility. The mobility of electrons may also be increased by providing a silicon layer having a tensile stress.

Third, the mobility of electrons and holes in the channel region of a field effect transistor may depend on the orientation of the length direction of the channel relative to the crystal lattice of a substrate wherein the channel region is formed. It has been found that, in N-type field effect transistors, a relatively high mobility of electrons may be obtained if the transistors are formed on an {001} surface of a silicon substrate. In P-type field effect transistors, however, a greater mobility of the holes in the channel region may be obtained if the transistors are formed on an {011} surface of a silicon substrate. Therefore, it has been proposed to form an integrated circuit in a semiconductor structure comprising a first and a second substrate, wherein surfaces of the first and the second substrate on which field effect transistors are formed are oriented differently with respect to the crystal lattice of the respective substrate. This approach, which may also be combined with a reduction of the dopant concentration in the channel region and/or a provision of stress in the channel region, is commonly denoted as "hybrid orientation technique."

Figure 1A:
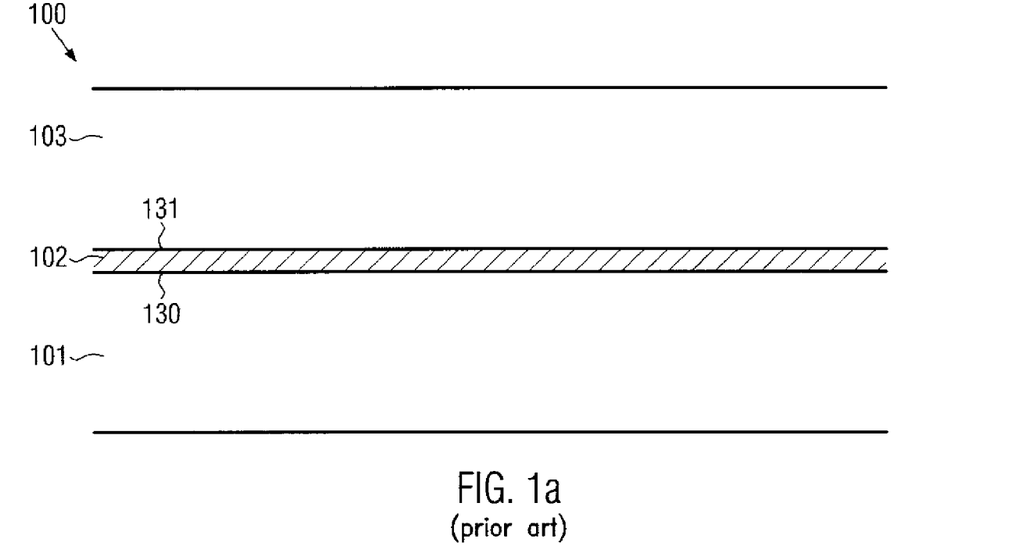
FIGS. 1a-1c show schematic cross-sectional views of a semiconductor structure in stages of a manufacturing process wherein a hybrid orientation technology according to the state of the art is employed.

An example of a method of manufacturing a semiconductor structure according to the state of the art employing hybrid orientation technique is described with reference to FIGS. 1a-1c. FIG. 1a shows a schematic cross-sectional view of a semiconductor structure 100 in a first stage of the manufacturing process according to the state of the art. The semiconductor structure 100 comprises a first substrate 101. The first substrate 101 comprises a surface 130 on which a layer 102 comprised of an electrically insulating material, such as silicon dioxide and/or silicon nitride, is formed. The first substrate 101 may be comprised of crystalline silicon and the surface 130 can be substantially a {001} surface.

A second substrate 103 is provided. The second substrate 103 may be comprised of the same material as the first substrate 101, for example crystalline silicon, and has a surface 131, the orientation of which relative to the crystal lattice of the second substrate is different from the orientation of the surface 130 relative to the crystal lattice of the first substrate 101. In examples of methods according to the state of the art wherein the surface 130 is substantially a {001} surface, the surface 131 can be substantially a {011} surface. The second substrate 103 is bonded to the first substrate 101. This can be done by means of wafer bonding techniques well known to persons skilled in the art, such as anodic bonding.

Figure 1B:
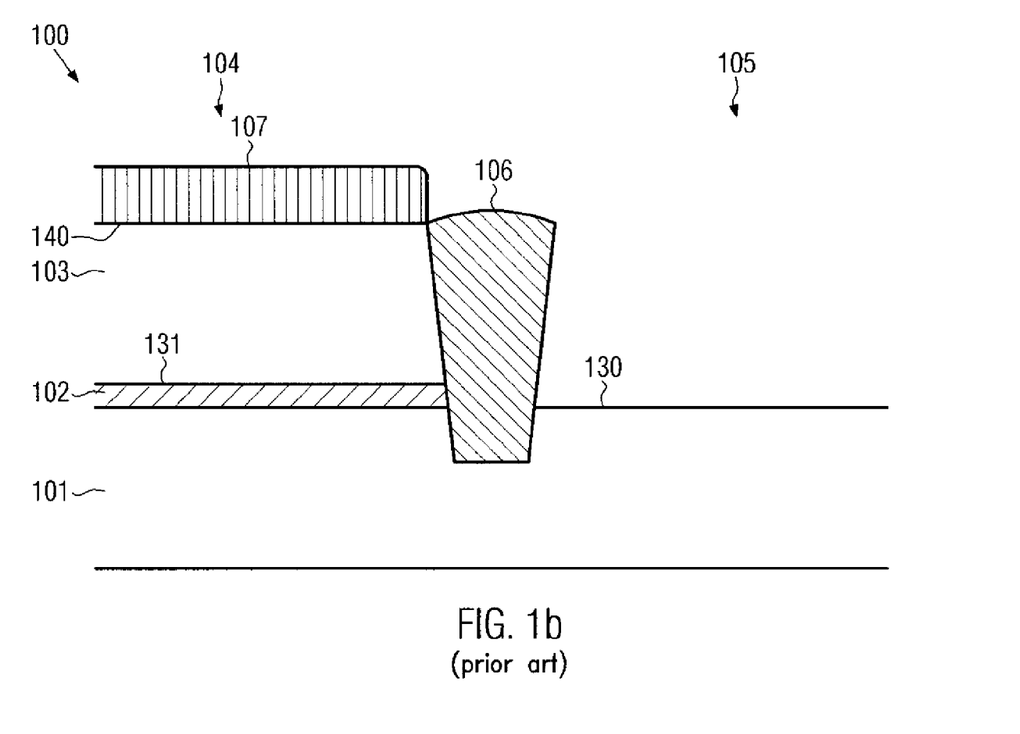

FIG. 1b shows a schematic cross-sectional view of the semiconductor structure 100 in a later stage of the manufacturing process. After bonding the second substrate 103 to the first substrate 101, a portion of the second substrate 103 is removed to obtain a smaller thickness of the second substrate 103. This can be done by cleaving the second substrate 103.

An implantation of hydrogen into the second substrate 103 may be performed before bonding the second substrate 103 to the first substrate 101. To this end, the surface 131 can be irradiated with hydrogen ions. The hydrogen ions penetrate the second substrate 103 and are stopped at a depth which may depend on the energy of the ions and their angle of incidence. Then, the ions are neutralized and incorporated into the second substrate 103. Ion energy and/or angle of incidence are adapted such that a moderately large amount of hydrogen is incorporated at a depth corresponding to the desired thickness of the portion of the second substrate 103 remaining on the first substrate. The presence of hydrogen reduces the mechanical stability of the second substrate 103. The cleaving process may, for example, be performed by directing a high pressure water jet to the semiconductor structure 100. Thereby, the second substrate 103 breaks apart at the depth to which the hydrogen was implanted.

When the second substrate 103 is cleaved, a surface 140 is formed at the side of the second substrate 103 opposite to the first substrate 101. An orientation of the surface 140 relative to the crystal lattice of the second substrate 103 may correspond to the orientation of the surface 131. For example, the surface 140 may be a $\{011\}$ silicon surface.

After cleaving the second substrate 103, a trench isolation structure 106 is formed in the semiconductor structure 100. The trench isolation structure 106 provides electrical insulation between a first portion 104 and a second portion 105 of the semiconductor structure 100. In the formation of the trench isolation structure 106, methods of photolithography, etching, oxidation and/or deposition well known to persons skilled in the art may be employed.

Thereafter, a mask layer 107, which may, for example, comprise silicon dioxide, is formed over the second substrate 103. This can be done by means of known deposition processes such as chemical vapor deposition (CVD) and/or plasma enhanced chemical vapor deposition (PECVD). Alternatively, the mask layer 107 may be formed by oxidizing a portion of the second substrate 103 at its surface. The reduction of thickness of the second substrate 103 may be taken into account in advance by correspondingly providing the second substrate 103 with a greater thickness.

In the second portion 105 of the semiconductor structure 100, the mask layer 107, the second substrate 103 and the layer 102 of electrically insulating material are removed. This can be done by means of known techniques of photolithography and etching.

Figure 1C:
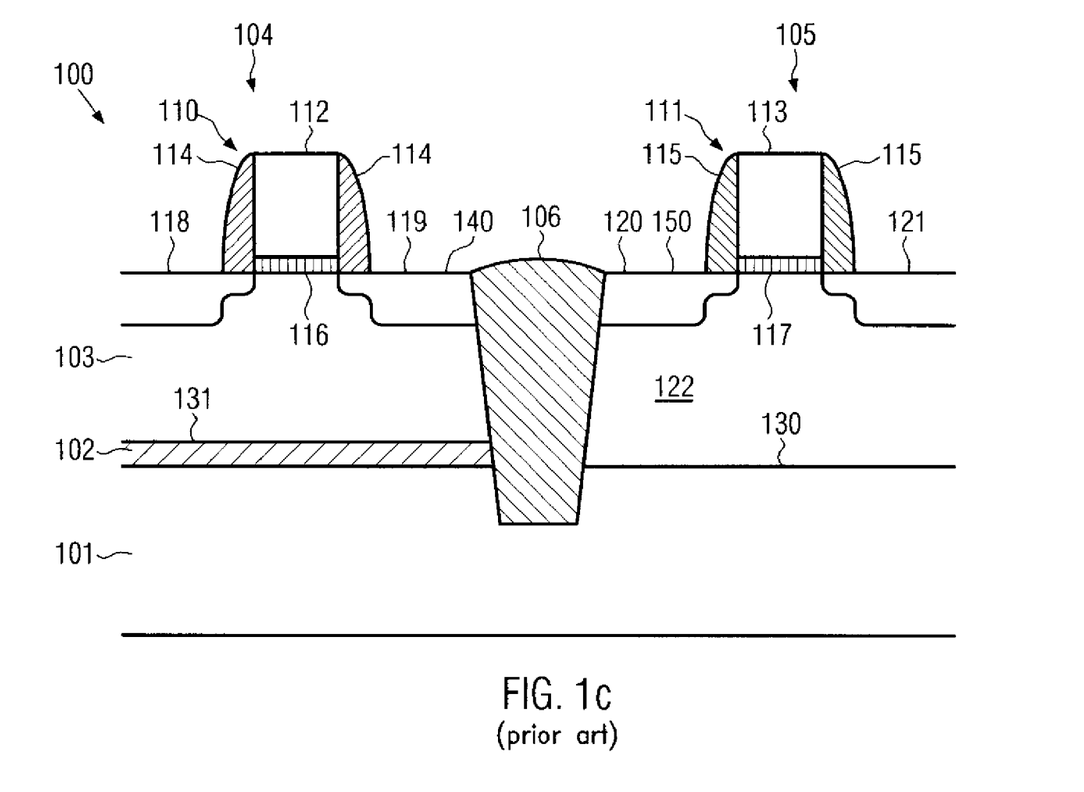

A schematic cross-sectional view of the semiconductor structure 100 in a further stage of the manufacturing process is shown in FIG. 1c. A selective epitaxial growth process is performed in order to form a material layer 122 over the second portion 105 of the semiconductor structure 100. As persons skilled in the art know, selective epitaxial growth is a variant of plasma enhanced chemical vapor deposition wherein parameters of the deposition process are adapted such that material is deposited only on the surface 130 of the first substrate 101 exposed in the second portion 105 of the semiconductor structure 100, whereas substantially no material deposition occurs on the surface of the trench isolation structure 106 and the mask layer 107. The material layer 122 may comprise the same material as the first substrate 101. In the formation of the material layer 122, the crystal structure of the material layer 122 adapts to that of the underlying first substrate 101. Therefore, a surface 150 of the material layer 122 has substantially the same orientation as the surface 130 of the first substrate 101.

Then, the mask layer 107 is removed and a first transistor element 110 and a second transistor element 111 are formed in the first 104 and the second 105 portion of the semiconductor structure 100, respectively. This can be done by means of processes well known to persons skilled in the art.

The first transistor element 110 comprises a gate electrode 112 separated from the second substrate 103 by a gate insulation layer 116 and flanked by a sidewall spacer structure 114. Adjacent the gate electrode 112, a source region 118 and a drain region 119 are formed. In examples of manufacturing processes according to the state of the art wherein the surface 140 of the second substrate 103 is a silicon $\{011\}$ surface, the first transistor element 110 can be a P-type field effect transistor.

Similar to the first transistor element 110, the second transistor element 111 comprises a gate electrode 113 separated from the material layer 122 by a gate insulation layer 117 and flanked by a sidewall spacer structure 115 as well as a source region 120 and a drain region 121. In examples of manufacturing processes according to the state of the art wherein the surface 150 of the material layer 122 is a silicon $\{001\}$ surface, the second transistor element 111 can be an N-type field effect transistor.

A problem of the method of manufacturing a semiconductor structure according to the state of the art is that the performance of the semiconductor structure 100 may critically depend on the accuracy of alignment of the first transistor element 110 to the crystal lattice of the second substrate 103 and the accuracy of alignment of the second transistor element 111 to the crystal lattice of the material layer 122. The accuracy of alignment of the first transistor element 110 and the second transistor element 111 may depend on the relative orientation of the crystal lattices of the second substrate 103 and the material layer 122, wherein the orientation of the crystal lattice in the material layer 122 is substantially identical to that of the crystal lattice of the first substrate 101. In photolithographic processes and other processes which are performed in the manufacturing of the first transistor element 110 and the second transistor element 111, it may be difficult to compensate any misalignment between the first substrate 101 and the second substrate 103.

The present disclosure is directed to various methods that may avoid, or at least reduce, the effects of one or more of the problems identified above.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

According to an illustrative embodiment disclosed herein, a method comprises providing a semiconductor structure comprising a first crystalline substrate and a second crystalline substrate. The semiconductor structure is irradiated with a radiation. Both the first crystalline substrate and the second crystalline substrate are exposed to the radiation. At least one diffraction pattern of a crystal lattice of the first crystalline substrate and a crystal lattice of the second crystalline substrate is measured. A relative orientation of the crystal lattice of the first crystalline substrate and the crystal lattice of the second crystalline substrate is determined from the at least one diffraction pattern.

According to another illustrative embodiment disclosed herein, a method comprises providing a semiconductor structure comprising a first crystalline substrate and a second crystalline substrate. The first crystalline substrate and the second crystalline substrate comprise the same material. The semiconductor structure is irradiated with a radiation. A pole figure representing a dependence of an intensity of radiation reflected from a predetermined grate plane of the first and second crystalline substrate on an orientation of the semiconductor structure relative to a direction of incidence of the radiation is determined from radiation diffracted from the semiconductor structure. In the pole figure, a position of at least one reflex from the first substrate and a position of at least one second reflex from the second substrate is determined. A relative orientation between a crystal lattice of the first substrate and a crystal lattice of the second substrate is calculated from the position of the at least one first reflex and the position of the at least one second reflex.

According to yet another illustrative embodiment disclosed herein, a method comprises providing a semiconductor structure comprising a first crystalline substrate and a second crystalline substrate. The semiconductor structure is irradiated with a radiation. An intensity of radiation diffracted from the semiconductor structure is measured. From the measured intensity, a first reciprocal space map comprising at least one first reflex from a grate plane of a crystal lattice of the first crystalline substrate and a second reciprocal space map comprising at least one second reflex from a grate plane of a crystal lattice of the second crystalline substrate is determined. A relative orientation between the crystal lattice of the second substrate and the crystal lattice of the first substrate is determined based on a position of the at least one first reflex and a position of the at least one second reflex.

BRIEF DESCRIPTION OF THE DRAWINGS

The disclosure may be understood by reference to the following description taken in conjunction with the accompanying drawings, in which like reference numerals identify like elements, and in which.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures, systems and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Embodiments of the subject matter disclosed herein provide methods which allow determining the relative orientation of the respective crystal lattices of a first substrate and a second substrate in a semiconductor structure. To this end, the diffraction of a radiation, such as x-rays and/or electrons and/or neutrons, at the semiconductor structure is investigated. While, in some embodiments, an angle of rotation between a specified lattice direction in the first substrate and a corresponding lattice direction in the second substrate can be determined, in other embodiments, a tilt between a first predetermined grate plane in the first substrate and a second predetermined grate plane in the second substrate may be investigated.

Thus, an accuracy of the alignment between the first substrate and the second substrate may be investigated before further process steps such as those employed in the formation of field effect transistors on the first and second substrate are performed. Hence, time and cost for these additional process steps may be saved. Methods according to the subject matter disclosed herein may be performed, for example, by manufacturers of wafers comprising bonded substrates to increase the quality of such wafers, or may be used by manufacturers of integrated circuits in order to check incoming material.

Figure 2A:
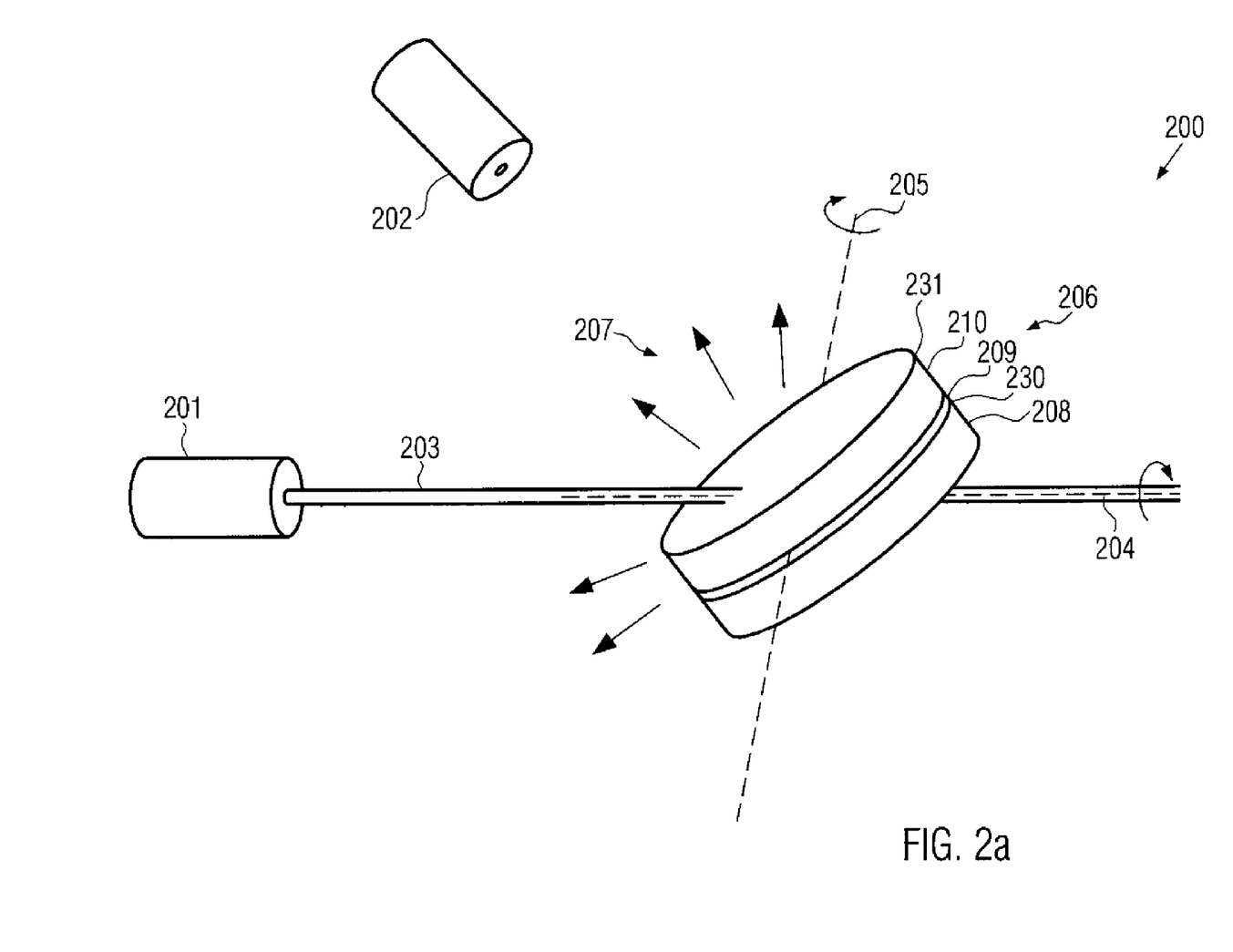
FIG. 2a shows a schematic perspective view of an apparatus which may be used in a method according to an illustrative embodiment disclosed herein.

FIG. 2a shows a schematic perspective view of an apparatus 200 which may be used in a method according to an embodiment disclosed herein. The apparatus 200 comprises a radiation source 201 adapted to emit a radiation 203. In some embodiments, the radiation source 201 can be an x-ray radiation source, for example, an x-ray tube of a type well known to persons skilled in the art. In other embodiments, the radiation source 201 can be adapted to emit a particle radiation, such as electrons and/or neutrons.

The apparatus 200 further comprises a detector 202 adapted to detect radiation of the type emitted by the radiation source 201. Hence, in embodiments wherein the radiation source 201 is configured to emit x-rays, the detector 202 can be an x-ray detector, for example, a semiconductor detector of a known type or a Geiger tube, whereas, in other embodiments in which the radiation 203 comprises particles such as electrons or neutrons, the detector 202 can be adapted to detect particles of the respective type.

The apparatus 200 can further comprise means for rotating (not shown) a semiconductor structure 206 around a first axis 204 and a second axis 205, which may be provided in the form of a goniometer of a type known to persons skilled in the art. In some embodiments, the radiation source 201, the detector 202 and the means for rotating the semiconductor structure 206 can be components of an x-ray diffraction measurement tool well known to persons skilled in the art.

Figure 2B:
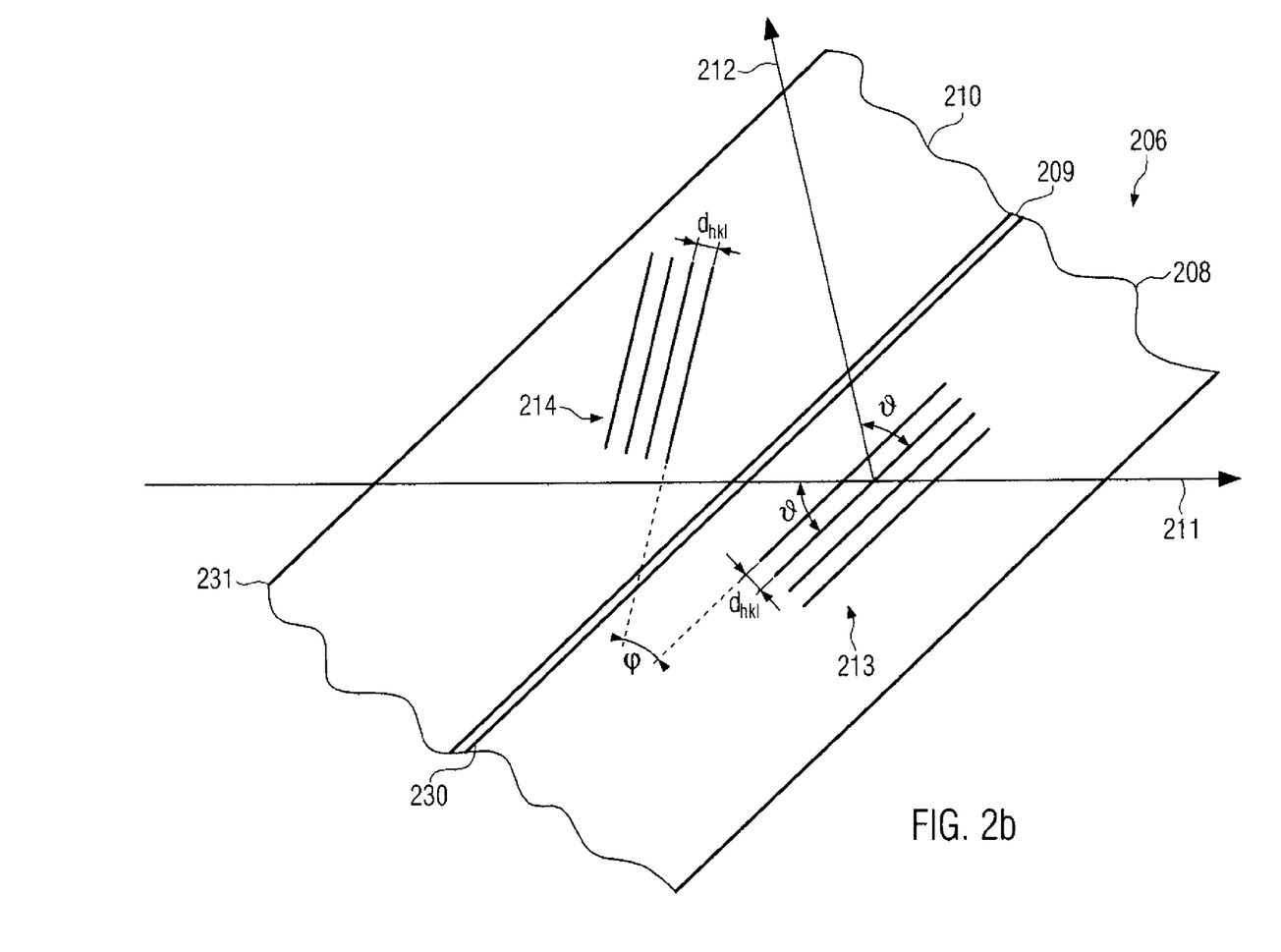
FIG. 2b shows a schematic cross-sectional view of a semiconductor structure illustrating grate planes in a first and a second substrate.
Figure 2C:
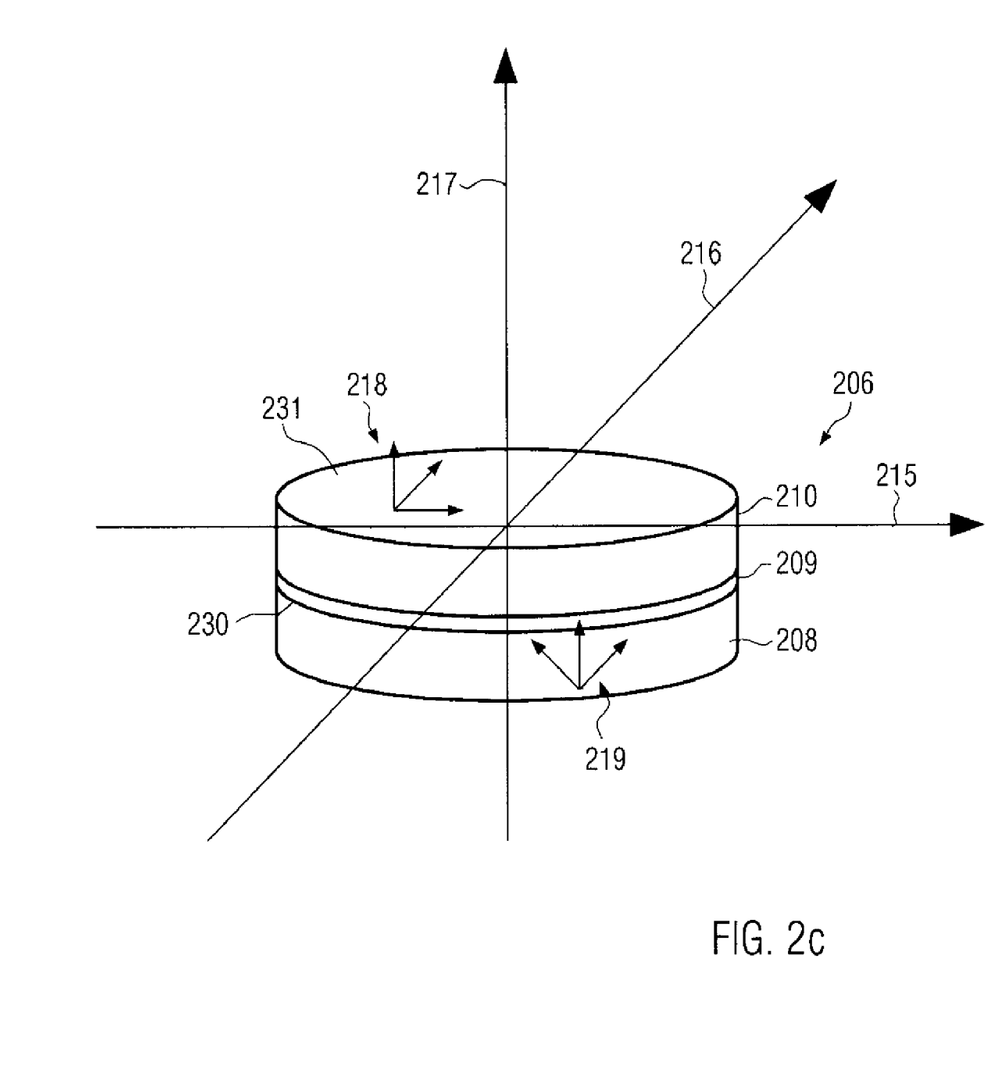
FIG. 2c shows a schematic perspective view of a semiconductor structure illustrating a relative orientation between a first and a second substrate.

Similar to the semiconductor structure 100 described above with reference to FIGS. 1a-1c, the semiconductor structure 206 comprises a first substrate 208 and a second substrate 210, which may be bonded to each other. A layer 209 of an electrically insulating material, such as silicon dioxide or silicon nitride, may be provided between the first substrate 208 and the second substrate 210. In other embodiments, however, the second substrate 210 may be directly bonded to the first substrate 208 without there being an electrically insulating layer 209 separating the substrates 208, 210. A schematic cross-sectional view of the semiconductor structure 210 is shown in FIG. 2b, whereas a schematic perspective view of the semiconductor structure 210 is shown in FIG. 2c.

The first substrate 208 comprises a first surface 230 on which the layer 209 of electrically insulating material and/or the second substrate 210 are provided. The second substrate 210 comprises a second surface 231. The second surface 231 can be formed on a side of the second substrate 210 opposite to the first substrate 208 and may be substantially parallel to the first surface 230.

The first substrate 208 and the second substrate 210 may have a crystalline structure and may be comprised of a same material. The crystalline orientation of the first surface 230 may be different from the crystalline orientation of the second surface 231. In FIG. 2c, reference numeral 219 denotes lattice vectors of the crystal lattice of the first substrate 208, whereas reference numeral 218 denotes lattice vectors of the crystal lattice of the second substrate 210. The lattice vectors 218 have a different orientation than the lattice vectors 219, while the first surface 230 and the second surface 231 are substantially parallel to each other. Coordinate axes 215, 216, 217 may be used to characterize the relative orientation of the first substrate 208 and the second substrate 210, as will be explained in more detail below.

In some embodiments disclosed herein, the first substrate 208 and the second substrate 210 may comprise silicon. In such embodiments, the first surface 230 may be substantially a {001} surface, while the second surface 231 can be substantially a {011} surface.

The radiation 203 output by the radiation source 201 is directed towards the semiconductor structure 200. The radiation 203 may penetrate at least one of the first substrate 208 and the second substrate 210, such that both substrates 208, 210 are exposed to the radiation 203. A portion of the radiation 203 is diffracted at the semiconductor structure 206, as schematically indicated by arrows 207 in FIG. 2a.

The intensity of the diffracted radiation 207 may have a directional dependency, such that an intensity of diffracted radiation measured by detector 202 may depend on the position of the detector 202 relative to the semiconductor structure 206. As persons skilled in the art know, the directional dependency of the diffracted radiation may be induced by the arrangement of atoms in the crystal lattices of the first substrate 208 and the second substrate 210.

In FIG. 2b, reference numeral 213 indicates grate planes of the crystal lattice of the first substrate 208, while reference numeral 214 indicates grate planes of the crystal lattice of the second substrate 210. The grate planes 213, 214 are characterized by the same Miller indices {hkl}, such that there is a substantially same spacing $d_{hkl}$ between the grate planes 213 and between the grate planes 214. Due to the different orientation of the crystal lattice of the first substrate 208 and the crystal lattice of the second substrate 210, the grate planes 213, 214 are rotated by an angle φ relative to each other.

As persons skilled in the art know, radiation having a wavelength λ is diffracted from grate planes having a spacing $d_{hkl}$ towards the detector 202 if an angle υ of incidence between the direction 211 of the incident radiation 203 and the grate planes 213 is equal to an angle between the grate planes and the direction 212 from the semiconductor structure 206 to the detector 202 and the wavelength λ, the angle υ and the distance $d_{hkl}$ between the grate planes fulfill a Bragg condition $$2d_{hkl}\sin\frac{\vartheta}{2} = m\lambda$$

wherein m is an integer number greater than zero. If the Bragg condition is fulfilled, a relatively high intensity of diffracted light can be measured by the detector 202, whereas otherwise there is destructive interference between the partial waves emitted by the individual atoms of the crystal such that only a relatively low intensity of diffracted light may be measured by the detector 202.

In some embodiments disclosed herein, an arrangement of the radiation source 201 and the detector 202 may be adapted such that the Bragg condition may be fulfilled for a particular grate plane of the material to be investigated, provided that the grate planes are arranged such that there is an equal angle υ between the incident radiation and the grate planes as well as between the grate planes and the direction from the semiconductor structure 206 to the detector 202. To this end, the direction 211 of the incident radiation 203 and the direction from the semiconductor structure 206 to the detector 202 may include an angle 180° −2υ wherein υ fulfills the Bragg condition. Equality of the angle between the direction 211 and the grate planes 213, 214 and the angle between the grate planes 213, 214 and the direction 212 may then be obtained by varying the orientation of the semiconductor structure 206, for example by rotating the semiconductor structure 206 around one or both of the axes 204, 205.

In some embodiments, the radiation source 201 and the detector 202 may be arranged such that the Bragg condition can be fulfilled for grate planes of a silicon crystal having Miller indices {hkl}={011}, wherein the integer m is equal to 4. The wavelength λ may be equal to the wavelength of the $K_\alpha$ line of copper which is about 1.54 Å. As persons skilled in the art know, x-rays having such a wavelength may be conveniently created by means of an x-ray tube comprising an anticathode made of copper.

In some embodiments, the semiconductor structure 206 may be rotated around the first axis 204 and the second axis 205 while being irradiated with the radiation 203 to vary the orientation of the semiconductor structure 206 relative to the radiation source 201 and the detector 202. The detector 202 is operated to record the intensity of diffracted light in dependence of the orientation of the semiconductor structure 206, which may be characterized by values of an angle of rotation of the semiconductor structure 206 around the axis 204 and an angle of rotation of the semiconductor structure 206 around the axis 205.

Values of the measured intensity of diffracted light may be shown in a diagram representing the intensity of diffracted light in dependence of the angles of rotation around the axis 204 and the axis 205. As persons skilled in the art know, this type of diagram is commonly denoted as "pole figure."

Figure 3:
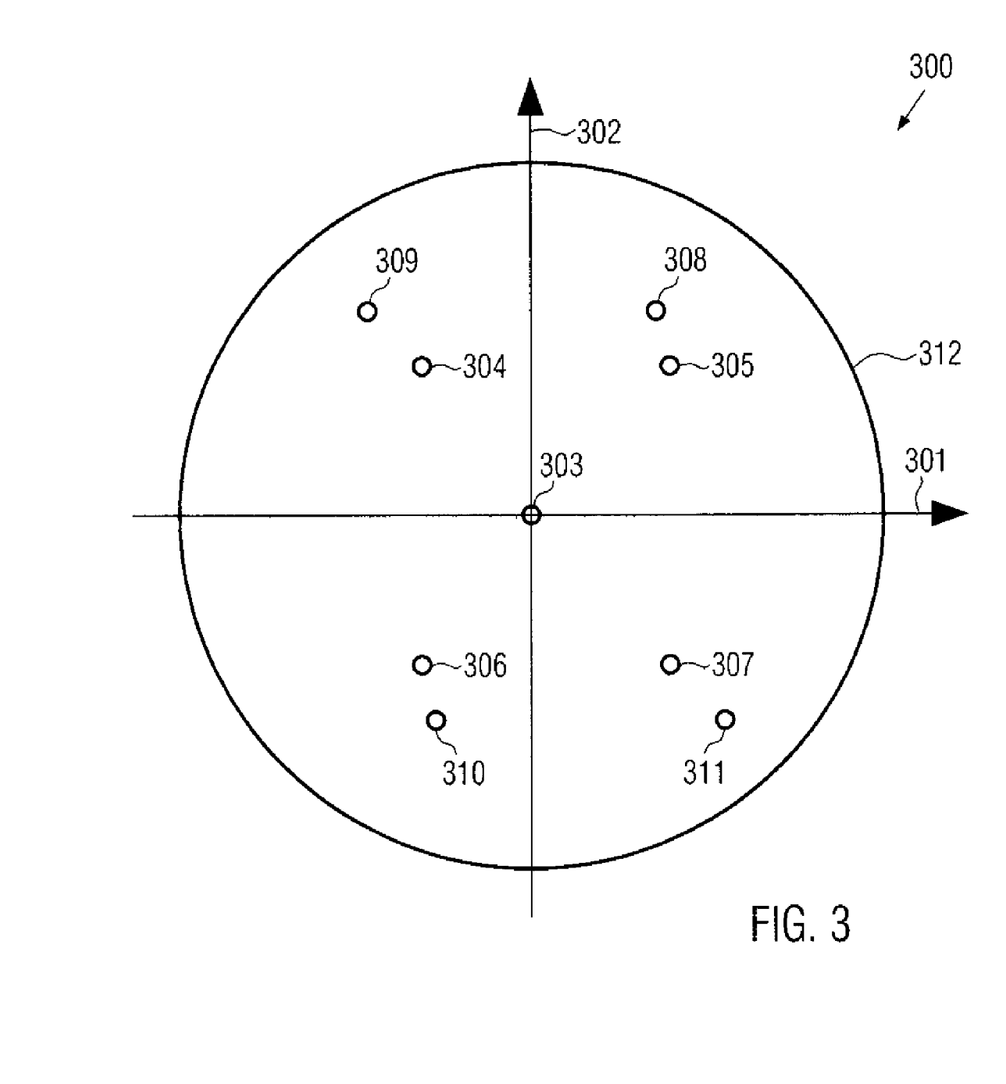
FIG. 3 shows a schematic illustration of a pole figure.

FIG. 3 depicts a schematic illustration of a pole FIG. 300 which may be obtained by investigating the semiconductor structure 206 in an embodiment wherein the surface 230 of the first substrate 208 is substantially a {001} surface and the surface 231 of the second substrate 210 is substantially a {011} surface, and wherein the detector location is adapted such that the Bragg condition is fulfilled for the {011} grate plane and m=4.

In the pole FIG. 300, a coordinate system is provided by a first coordinate axis 301 representing values of an angle of rotation of the semiconductor structure 206 around a first axis and a second coordinate axis 302 representing values of an angle of rotation of the semiconductor structure 206 around a second axis. In some embodiments, the coordinate system may comprise a stereographic projection of the angular distribution of the intensity of the diffracted radiation measured by the detector 202. The angles of rotation may be transformed such that a position of the semiconductor structure 206 wherein the Bragg condition is fulfilled for radiation 203 diffracted towards the detector 202 by a predetermined grate plane of the crystal lattice of the second substrate 206 being substantially parallel to the surface 231 of the second substrate is located at the origin of the coordinate system provided by the first coordinate axis 301 and the second coordinate axis 302. Hence, at the origin, a reflex 303, wherein a high intensity of diffracted light is measured, can be obtained. In some embodiments wherein the second surface 231 of the second substrate 210 is substantially a silicon {011} surface, the origin of the coordinate system may correspond to a position of the semiconductor structure 206 at which radiation diffracted from a {011} grate plane towards the detector 202 fulfills the Bragg condition.

Due to the symmetry of the crystal lattice of the second substrate 210, further reflexes 308, 309, 310, 311 of further {011} grate planes in the crystal lattice of the second semiconductor substrate 206 may be obtained. The positions of such further reflexes may help to determine the orientation of one or more specific lattice directions in the crystal lattice of the second substrate 210. For example, the orientation of a <011> direction of the crystal lattice of the second substrate 210 may be calculated. Such calculations may be performed by means of methods known to persons skilled in the art.

Since the radiation 203 is also diffracted by the first substrate 208, the pole FIG. 300 also comprises reflexes 304, 305, 306, 307 which are created by grate planes in the first substrate 208. The positions of the reflexes 304, 305, 306, 307 from the first substrate 208 may be determined and an orientation of one or more specific lattice directions of the crystal lattice of the first substrate 208 corresponding to the one or more specific lattice directions, the orientation of which was determined for the crystal lattice of the second substrate 210, may be calculated from the positions of the reflexes 304, 305, 306, 307. Methods known to persons skilled in the art may be used for such calculations.

From the orientation of the one or more specific lattice directions in the first substrate 208 and the second substrate 210, the relative orientation of the crystal lattice of the first crystalline substrate and the crystal lattice of the second crystalline substrate may then be determined. In particular, the relative orientation between the first substrate 208 and the second substrate 210 may comprise an angle of rotation of the <011> direction of the crystal lattice of the second substrate 210 around a vertical axis 217 (FIG. 2c) substantially perpendicular to the surfaces 230, 231 of the first substrate and the second substrate, the angle of rotation being measured relative to the <011> direction of the crystal lattice of the first substrate 208. The angle of rotation between the <011> direction of the second substrate 210 and the <011> direction of the first substrate 208 may be determined with an accuracy of about 1° or less.

Figure 4:
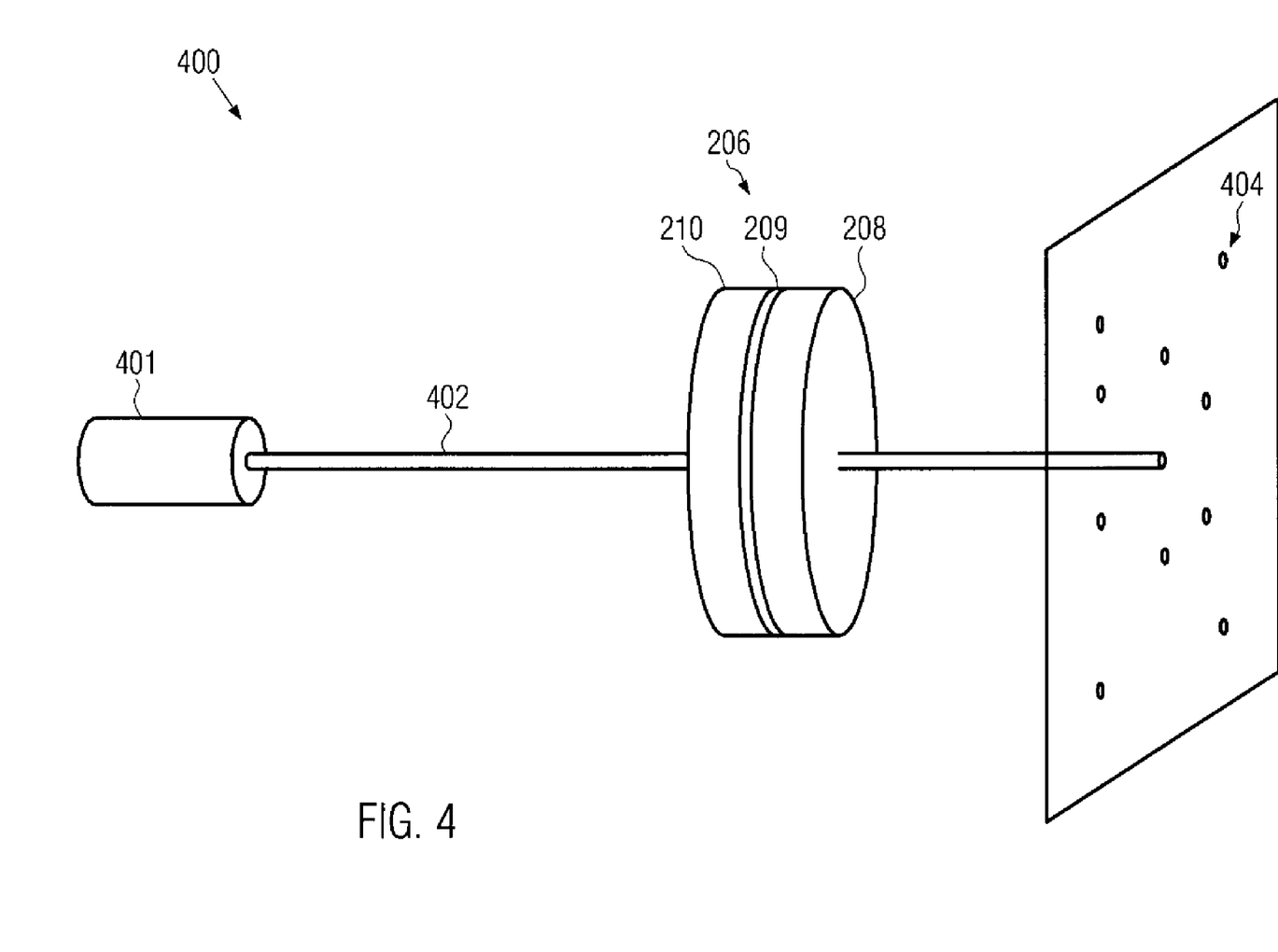
FIG. 4 shows a schematic perspective view of an apparatus which may be used in a method according to an illustrative embodiment disclosed herein.

FIG. 4 shows a schematic perspective view of an apparatus 400 which may be used in a method according to another embodiment. The apparatus 400 comprises a radiation source 401 adapted to provide a radiation 402 which may be directed to the semiconductor structure 206. While, in some embodiments, the radiation 402 may comprise x-rays, in other embodiments, the radiation 402 may comprise electrons and/or neutrons. In some embodiments, the radiation 402 may comprise electrons and/or neutrons in addition to x-rays.

The apparatus 400 further comprises a detector 404 adapted to detect radiation emitted by the radiation source 401 and diffracted by the semiconductor structure 206. The detector 404 may be provided in the form of a photographic plate or film as well as in the form of a semiconductor detector, Geiger tube or any other type of detector being sensitive to the type of radiation emitted by the radiation source 401. While, in some embodiments, the detector 401 may be movable relative to the radiation source 401 and/or the semiconductor structure 206, in other embodiments, the detector 401 may be provided at a fixed position relative to the radiation source 401 and/or the semiconductor structure 206.

In a method disclosed herein, a first reciprocal space map comprising at least one reflex from a grate plane of the crystal lattice of the first substrate 208 of the semiconductor structure 206 is determined.

In some embodiments, the first reciprocal space map may comprise a Laue diagram. As persons skilled in the art know, in the determination of a Laue diagram by means of x-ray diffraction, radiation 402 comprising a plurality of wavelengths are directed to the semiconductor structure 206. At grate planes of the crystal lattice of the second substrate, x-rays are reflected towards the detector 404, provided that, for one of the plurality of wavelengths, the distance between adjacent grate planes and the relative orientation of the first substrate 208 and the detector 404 fulfill a Bragg condition.

In other embodiments, the radiation 402 emitted by the radiation source 401 can comprise substantially monochromatic radiation, for example x-rays having a wavelength of about 1.54 Å, which may be conveniently created by means of an x-ray tube comprising an anticathode made of copper. In such embodiments, the detector 404 and/or the semiconductor structure 206 may be moved relative to each other in order to determine the first reciprocal space map.

In the first reciprocal space map, the position of the at least one reflex from the first substrate 208 is identified and an orientation of the crystal lattice of the first semiconductor structure 208 is determined from the position of the at least one reflex. To this end, methods known to persons skilled in the art of x-ray diffraction may be employed.

A second reciprocal space map comprising at least one reflex from a grate plane of the crystal lattice of the second substrate 210 is determined.

In some embodiments, the first reciprocal space map and the second reciprocal space map may be recorded simultaneously. To this end, the first substrate 208 and the second substrate 210 may be simultaneously exposed to the radiation 402 emitted by the radiation source 401. Reflexes from the crystal lattice of the first substrate 208 and reflexes from the crystal lattice of the second substrate 210 may be identified based on an estimate of the relative orientation of the crystal lattices of the first 208 and the second 210 substrate, wherein the estimate may be based on a desired orientation of the crystal lattices.

In other embodiments, the first reciprocal space map and the second reciprocal space map may be determined successively. In such embodiments, in the determination of the first reciprocal space map, the radiation 402 may be selectively directed to the first substrate 208, and in the determination of the second reciprocal space map, the radiation 402 may be selectively directed to the second substrate 208. To this end, the semiconductor structure 206 may first be oriented such that the radiation 402 impinges on the first substrate 208 from a lateral direction substantially parallel to the first surface 230 while the first reciprocal space map is determined. Thereafter, the semiconductor structure 206 is moved, for example in a direction substantially parallel to the first surface 230, such that the radiation 402 impinges on the second substrate 210 from the lateral direction. The motion of the semiconductor structure 206 may substantially not comprise a rotation of the semiconductor structure 206 such that angles between grate planes and the direction of incidence of the radiation 402 remain substantially unaltered during the measurement of the first and the second reciprocal space map. Thus, an offset of angles of rotation of the semiconductor structure 206 is not altered by the motion of the semiconductor structure 206.

In other embodiments, radiation of a different type may be used in order to determine the first reciprocal space map and the second reciprocal space map. For example, x-rays may be used in order to determine the first reciprocal space map and electrons can be used in order to determine the second reciprocal space map, as will be explained in more detail below.

A relative orientation between the crystal lattice of the first substrate 208 and the crystal lattice of the second substrate 210 may be determined from the first reciprocal space map and the second reciprocal space map.

To this end, a theoretical position of at least one reflex from a grate plane of the crystal lattice of the second substrate can be determined for a desired relative orientation between the crystal lattice of the first substrate and the crystal lattice of the second substrate and the determined orientation of the crystal lattice of the first substrate. For example, in some embodiments, it may be desirable that the first substrate 208 has a first surface 230 substantially parallel to a silicon {001} grate plane and the second substrate 210 has a second surface 231 substantially parallel to a silicon {011} grate plane. The theoretical position of the at least one reflex from the grate plane of the crystal lattice may be calculated from the Bragg conditions or from corresponding Laue equations well known to persons skilled in the art.

Thereafter, a deviation between the theoretical position of the at least one reflex from the grate plane of the second substrate and a measured position of the at least one reflex determined from the second reciprocal space map is determined. The relative orientation of the crystal lattice of the first substrate and the crystal lattice of the second substrate may then be calculated from the deviation between the theoretical position of the at least one reflex and the measured position of the at least one reflex, for example by solving Bragg equations and/or Laue equations for one or more grate planes corresponding to the at least one reflex for parameters characterizing the relative orientation of the first substrate 208 and the second substrate 210.

In some embodiments, the relative orientation between the crystal lattices of the first substrate 208 and the second substrate 210 may be determined in terms of a tilt of a <011> axis of the first substrate relative to a <001> axis of the second substrate. The tilt can be expressed by a first angle of rotation around a first axis 215 and a second angle of rotation around a second axis 216 (FIG. 2c). Since, in a silicon crystal, the <001> axis is substantially perpendicular to the {001} grate plane and the <011> axis is substantially perpendicular to the {011} grate plane, the tilt between the <001> axis and the <011> axis is representative for the tilt between the {011} grate plane in the second substrate and the {001} grate plane in the first substrate.

The above method enables one to determine the tilt between {011} grate planes in the second substrate 210 and the {001} grate planes in the first substrate 208 with an accuracy of about 0.05°.

In some embodiments, methods of determining a relative orientation of the crystal lattice of the first substrate 208 and the crystal lattice of the second substrate 210 may be performed before a cleaving process similar to that employed in the method of manufacturing a semiconductor structure described above with reference to FIGS. 1a-1c is performed. Advantageously, this may help obtain a greater intensity of reflexes from the second semiconductor substrate 210, since a greater thickness of material of the second substrate 210 is present in the semiconductor structure 206. In other embodiments, however, the second substrate 210 may be cleaved before determining the relative orientation of the crystal lattices of the first substrate 208 and the second substrate 210. In some of these embodiments, field effect transistor elements similar to the field effect transistor elements 110, 111 in the semiconductor structure 100 described above with reference to FIGS. 1a-1c may be formed over the first substrate 208 and the second substrate 210 before the relative orientation of the crystal lattices is determined.

In some embodiments, the radiation 203, 402 directed to the semiconductor structure 206 may comprise both x-rays and electrons. The semiconductor structure 206 may be oriented relative to the direction of incidence of the radiation such that the radiation first impinges on the surface 231 of the second substrate 210, whereas the radiation reaches the first substrate 208 only after penetrating the second substrate 210.

The interaction between crystalline matter and electrons having a wavelength of the same order of magnitude as the distance of atoms in the crystal lattice can be stronger than the interaction between the crystalline matter and x-rays the wavelength of which has the same order of magnitude. Hence, even in case the second substrate 210 is relatively thin, for example because a cleaving process has been performed before the investigation of the semiconductor structure 206, a relatively high intensity of electrons diffracted from the second substrate 210 may be observed. Since a relatively large fraction of the electrons may be absorbed in the second substrate 210 even in the case of a relatively small thickness of the second substrate 210, a relatively low intensity of electrons diffracted from the first substrate 208 can be observed. The x-rays, however, may penetrate the second substrate 210 and are diffracted in the first substrate 208.

Thus, the intensity of diffracted electrons may be used in order to determine the orientation of the crystal lattice of the second substrate 210, whereas the intensity of diffracted x-rays may be used to determine the orientation of the crystal lattice of the first substrate 208. In such embodiments, two radiation sources and two detectors can be provided.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
    providing a semiconductor structure comprising a first crystalline substrate and a second crystalline substrate;
    irradiating said semiconductor structure with a radiation, wherein both said first crystalline substrate and said second crystalline substrate are exposed to said radiation;
    measuring at least one diffraction pattern of a crystal lattice of said first crystalline substrate and a crystal lattice of said second crystalline substrate; and
    determining a relative orientation of said crystal lattice of said first crystalline substrate and said crystal lattice of said second crystalline substrate from said at least one diffraction pattern.

2. The method of claim 1, wherein said radiation comprises x-rays.

3. The method of claim 1, wherein said first crystalline substrate and said second crystalline substrate are comprised of the same material.

4. The method of claim 3, wherein said measurement of said diffraction pattern comprises determining a pole figure.

5. The method of claim 4, wherein said determination of said pole figure comprises:
    providing a detector at a predetermined detector location, said detector location being selected such that a Bragg condition is fulfilled for said radiation when being diffracted from a predetermined grate plane of said first and second crystalline substrate towards said detector location;
    rotating said semiconductor structure around a first axis and a second axis to vary an orientation of said semiconductor structure; and
    operating said detector to record an intensity of diffracted radiation in dependence of said orientation of said semiconductor structure.

6. The method of claim 5, wherein said determination of said relative orientation of said crystal lattice of said first substrate and said crystal lattice of said second substrate comprises determining a position of reflexes from said first crystalline substrate and a position of reflexes from said second crystalline substrate.

7. The method of claim 1, wherein said measurement of said at least one diffraction pattern comprises:
    determining a first reciprocal space map comprising at least one reflex from a grate plane of said crystal lattice of said first substrate; and
    determining a second reciprocal space map comprising at least one reflex from a grate plane of said crystal lattice of said second substrate.

8. The method of claim 7, wherein said determination of said relative orientation of said crystal lattice of said first substrate and said crystal lattice of said second substrate comprises:
    determining an orientation of said crystal lattice of said first substrate based on said first reciprocal space map;
    calculating a theoretical position of at least one reflex from a grate plane of said crystal lattice of said second substrate for a desired relative orientation between said crystal lattice of said first substrate and said crystal lattice of said second substrate and said determined orientation of said crystal lattice of said first substrate; and
    determining said relative orientation of said crystal lattice of said first substrate and said crystal lattice of said second substrate based on a deviation between said theoretical position of said at least one reflex and a measured position of said at least one reflex determined from said second reciprocal space map.

9. The method of claim 3, wherein said first substrate comprises a first surface and said second substrate comprises a second surface, said second surface being substantially parallel to said first surface, an orientation of said first surface relative to said crystal lattice of said first substrate being different from an orientation of said second surface relative to said crystal lattice of said second substrate.

10. The method of claim 9, wherein said same material comprises silicon.

11. The method of claim 10, wherein said first surface is substantially a {001} surface and said second surface is substantially a {011} surface.

12. A method, comprising:
    providing a semiconductor structure comprising a first crystalline substrate and a second crystalline substrate, said first crystalline substrate and said second crystalline substrate comprising the same material;
    irradiating said semiconductor structure with a radiation;
    determining from radiation diffracted from said semiconductor structure a pole figure representing a dependence of an intensity of radiation reflected from a predetermined grate plane of said first and second crystalline substrate on an orientation of said semiconductor structure relative to a direction of incidence of said radiation;
    determining in said pole figure a position of at least one first reflex from said first substrate and a position of at least one second reflex from said second substrate; and
    calculating a relative orientation between a crystal lattice of said first substrate and a crystal lattice of said second substrate from said position of said at least one first reflex and said position of said at least one second reflex.

13. The method of claim 12, wherein said first crystalline substrate comprises a first surface and said second crystalline substrate comprises a second surface, said first surface and said second surface being substantially parallel to each other, an orientation of said first surface relative to said crystal lattice of said first substrate being different from an orientation of said second surface relative to said crystal lattice of said second substrate.

14. The method of claim 13, wherein said same material comprises silicon.

15. The method of claim 14, wherein said first surface is substantially a {001} surface and said second surface is substantially a {011} surface.

16. The method of claim 14, wherein said grate plane comprises a {011} plane.

17. The method of claim 14, wherein said relative orientation between said crystal lattice of said first substrate and said crystal lattice of said second substrate comprises an angle of rotation between a <011> direction of said crystal lattice of said first crystalline substrate and a <011> direction of said crystal lattice of said second crystalline substrate.

18. A method, comprising:
providing a semiconductor structure comprising a first crystalline substrate and a second crystalline substrate;
irradiating said semiconductor structure with a radiation;
measuring an intensity of radiation diffracted from said semiconductor structure;
determining from said measured intensity a first reciprocal space map comprising at least one first reflex from a grate plane of a crystal lattice of said first crystalline substrate and a second reciprocal space map comprising at least one second reflex from a grate plane of a crystal lattice of said second crystalline substrate; and
determining a relative orientation between said crystal lattice of said second substrate and said crystal lattice of said first substrate based on a position of said at least one first reflex and a position of said at least one second reflex.

19. The method of claim 18, wherein said first crystalline substrate and said second crystalline substrate are substantially comprised of silicon.

20. The method of claim 19, wherein said first crystalline substrate comprises a substantially {011} oriented first surface and said second crystalline substrate comprises a substantially {011} oriented second surface.

21. The method of claim 19, wherein said relative orientation between said crystal lattice of said second crystalline substrate and said crystal lattice of said first crystalline substrate comprises a tilt of a <011> axis of said second crystalline substrate relative to a <001> axis of said first crystalline substrate.

\* \* \* \* \*